United States Patent [19]
Levesque et al.

[11] Patent Number: 5,392,652
[45] Date of Patent: Feb. 28, 1995

[54] METHOD AND APPARATUS FOR INSPECTION OF METAL OBJECTS UTILIZING VARIABLE ANGLE ULTRASONIC TRANSDUCER

[75] Inventors: Kevin J. Levesque, Swainsboro, Ga.; David B. Richey, Benton City, Wash.

[73] Assignee: Lambert, MacGill, Thomas, Inc., Santa Clara, Calif.

[21] Appl. No.: 864,531

[22] Filed: Apr. 7, 1992

[51] Int. Cl.⁶ .................................... G01N 29/26
[52] U.S. Cl. .............................. 73/629; 73/632; 73/634
[58] Field of Search ............ 73/620, 627, 628, 629, 73/632, 633, 634, 635, 639

[56] References Cited

U.S. PATENT DOCUMENTS

| | | | |
|---|---|---|---|
| 3,791 | 10/1844 | Taylor | 241/262 |
| 1,189,501 | 7/1916 | Smith | 105/102 |
| 3,238,448 | 3/1966 | Wood et al. | 324/220 |
| 3,326,496 | 6/1967 | Auberson | 104/138.1 |
| 3,583,211 | 6/1971 | Brech et al. | 73/623 |
| 3,745,813 | 7/1973 | Vozumi | 73/639 |
| 3,766,775 | 10/1973 | Gunkel | 73/623 |
| 3,850,028 | 11/1974 | Tompson et al. | 73/643 |
| 3,898,838 | 8/1975 | Connelly | 73/634 |
| 3,916,676 | 11/1975 | Boggs et al. | 73/609 |
| 3,978,714 | 9/1976 | Shraiber et al. | 73/634 |
| 4,010,868 | 3/1977 | Clark et al. | 221/9 |
| 4,092,868 | 6/1978 | Thompson et al. | 73/638 |
| 4,102,206 | 7/1978 | Perdijon | 73/644 |
| 4,106,347 | 8/1978 | DeKerlegand | 73/622 |
| 4,126,491 | 11/1978 | Karlsson | 148/195 |
| 4,166,395 | 9/1979 | Dannehl | 73/634 |
| 4,173,898 | 11/1979 | Forstermann et al. | 73/611 |
| 4,175,224 | 11/1979 | Sims et al. | 219/60 R |
| 4,202,216 | 5/1980 | Bull et al. | 73/639 |
| 4,203,069 | 5/1980 | Davis | 324/220 |
| 4,212,207 | 7/1980 | Conradi | 73/623 |
| 4,213,183 | 7/1980 | Barron et al. | 364/507 |
| 4,229,796 | 10/1980 | Garrett | 364/507 |
| 4,261,034 | 4/1981 | Saccomano et al. | 395/275 |
| 4,262,331 | 4/1981 | Freeland et al. | 395/275 |
| 4,282,577 | 8/1981 | Abend et al. | 73/634 |
| 4,307,615 | 12/1981 | Robinson | 73/643 |
| 4,314,479 | 2/1982 | Spijkerman | 73/643 |
| 4,353,257 | 10/1982 | Vrba et al. | 73/623 |
| 4,375,165 | 3/1983 | de Sterke | 73/622 |
| 4,404,853 | 9/1983 | Livingston | 73/622 |
| 4,434,660 | 3/1984 | Michaels et al. | 73/622 |
| 4,453,410 | 12/1984 | Schmitz et al. | 73/640 |
| 4,475,394 | 10/1984 | Takeda et al. | 73/598 |
| 4,475,399 | 10/1984 | Livingston | 73/622 |

(List continued on next page.)

FOREIGN PATENT DOCUMENTS 2537613  10/1977  Germany ............................. 73/633

Primary Examiner—Hezron E. Williams
Assistant Examiner—Rose M. Finley
Attorney, Agent, or Firm—John J. Leavitt

[57] ABSTRACT

Presented is a method and apparatus for inspection through use of a variable angle ultrasonic transducer of metallic members such as pipes, conduits, plates and other formed metallic members normally having a surface regularity adhering to a predetermined standard of normalcy. Inspection proceeds in such a manner that irregularities in the surface of the member under test that lie outside the standard of normalcy are sensed, the degree of irregularity determined and converted into an electrical signal that is applied to continually variably control the angular relationship of the ultrasonic transducer with the surface of the metallic member being inspected whereby abnormalities within the metallic member may be reliably and accurately detected, displayed and recorded. In terms of apparatus, the ultrasonic transducer is provided with an arcuate sound transmitting surface, and the the transducer is mounted for pivotal rotation about an axis of rotation correlated to the radius of curvature of the arcuate sound transmitting surface. The transducer is also mounted for automatic axial and vertical displacement in relation to irregularities encountered during the test, with automatic pivotal rotation of the transducer being effected in correlation to the axial and vertical displacement.

21 Claims, 4 Drawing Sheets

U.S. PATENT DOCUMENTS

| | | | |
|---|---|---|---|
| 4,487,071 | 12/1984 | Pagano | 73/612 |
| 4,487,072 | 12/1984 | Livingston | 73/622 |
| 4,495,587 | 1/1985 | Plante et al. | 364/507 |
| 4,520,671 | 6/1985 | Hardin | 73/620 |
| 4,523,468 | 6/1985 | Derkacs et al. | 73/598 |
| 4,537,075 | 8/1985 | Jackson et al. | 73/634 |
| 4,541,064 | 9/1985 | Livingston | 364/552 |
| 4,663,727 | 5/1987 | Saporito et al. | 364/551.01 |
| 4,675,604 | 6/1987 | Moyer | 324/220 |
| 4,691,572 | 9/1987 | van den Berg et al. | 73/643 |
| 4,700,572 | 10/1987 | Senba et al. | 73/622 |
| 4,785,902 | 11/1988 | Ochiai | 180/164 |
| 4,872,130 | 10/1989 | Pagano | 364/507 |
| 4,885,995 | 12/1989 | Antosh | 104/118 |
| 4,909,091 | 3/1990 | Ellmann et al. | 73/866.5 |
| 4,995,320 | 2/1991 | Sato et al. | 104/118 |
| 5,043,663 | 8/1991 | Lam | 324/242 |

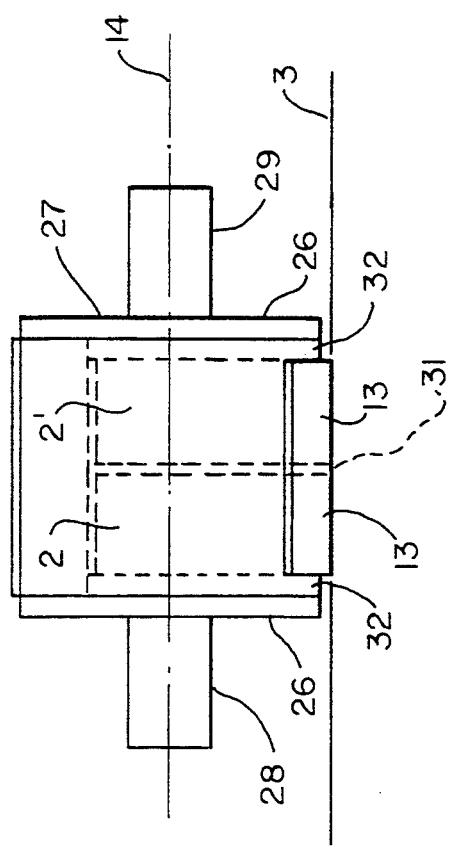
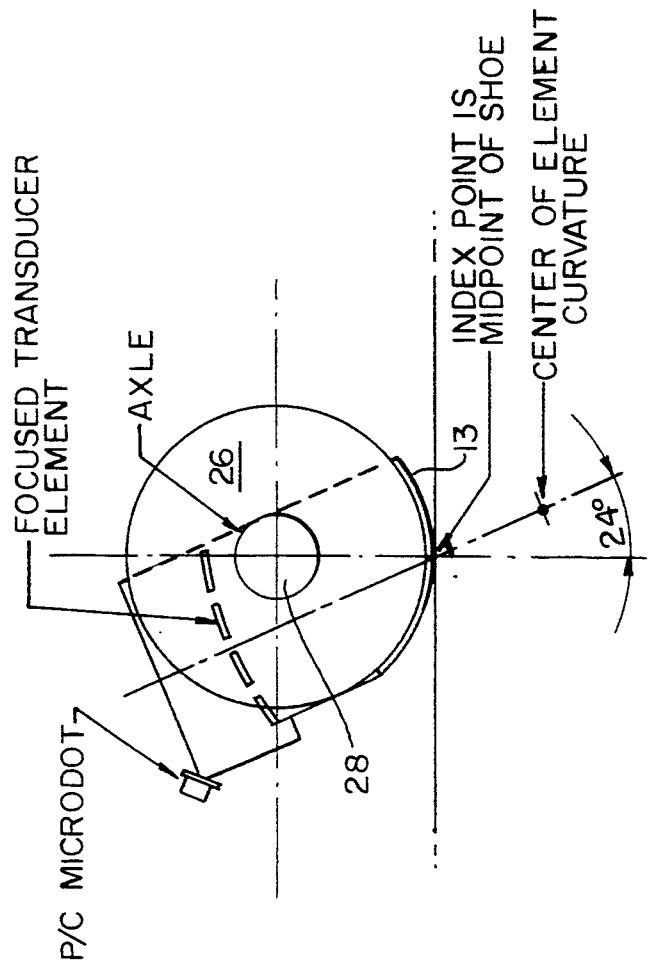
FIG. 4
FIG. 3

METHOD AND APPARATUS FOR INSPECTION OF METAL OBJECTS UTILIZING VARIABLE ANGLE ULTRASONIC TRANSDUCER

BACKGROUND OF THE INVENTION

1. Field of the Invention

This invention relates to ultrasonic transducers for performing inspections of the interior of metals, and more particularly to an ultrasonic transducer applicable to accurately inspect the interior of metal objects such as steel pipe having complex irregular surface areas.

2. Description of the Prior Art

A preliminary patentability and novelty search conducted in connection with the invention forming the subject matter herein revealed the existence of the following United States patents:

| | |
|---|---|
| 4,541,064 | 4,663,727 |
| 4,691,572 | 4,700,572 |
| 4,872,130 | 4,995,320 |
| 5,043,663 | |

The patents listed above are representative of the abundance of prior art patents that relate to the general subject of non-destructive testing or inspection of hollow cylindrical steel members, such as lengths of steel pipe used for containment of hot water and steam in atomic energy electric generating plants, boilers of the type used for generating steam for use in steam turbines for generating electricity, and steel tubing for well drilling, pumping and well casing, particularly in the oil and gas industry. Some of the physical characteristics tested for include wall thickness, there being very close tolerances regarding adherence to internal and external diameters, voids within the interior of the metal wall, cracks of various kinds, including circumferential, angular and longitudinal cracks that are difficult or impossible to detect by a mere visual inspection of the exterior or interior surface of the tubing or pipe. The reason it is important to detect and eliminate or repair tubing or pipe lengths having such defects stems from the fact that inclusion of a defective length of tubing or pipe in an installation may result in a rupture of the tubing or pipe, possibly resulting in catastrophic property damage, and perhaps even the loss of life among personnel working in the vicinity of the rupture.

As will be seen from the teachings of the patents listed above, such testing and inspection is frequently accomplished through application of ultrasonic technology. The broad concept of the utilization of ultrasonic wave energy for the detection of flaws within the interior of a body is of course an old concept in the prior art. The concept has been used to test lengths of rails to determine the existence of flaws to thus increase the reliability of railroad tracks. In more recent times, the concept has been combined with computer technology to provide visual and printed displays of the location and extent of "flaws" in such diverse objects as steel tubing, conduit, pipe lengths, and even the human body, where abnormalities within the body may be discovered without invasive surgical procedures.

In the area of testing and inspection of elongated lengths of steel tubing or pipes for flaws, such inspection may occur following manufacture and before installation, or it may occur after installation and use for a finite time followed by removal for the express purpose of inspection for damage that might having ocurred during installation or use, and prior to reinstallation. Thus, referring to U.S. Pat. No. 4,541,064, there is taught a method and apparatus for ultrasonic testing of tubular goods to discover the presence of defects, to determine the orientation of the defect, i.e., circumferential, angular or longitudinal, to determine its extent, and to display the defect through use of computer technology. The process proceeds without the need to rotate either the inspection head or the tubular goods being inspected. Instead, the inspecting head includes a full coverage transducer collar having arrays of ultrasonic transducers positioned to test for longitudinal, transverse and wall thickness defects, the transducers being operatively connected to a computer system programmed to display and or record the location, type and extent of the flaws as the transducer collar and test piece move relative to one another.

U.S. Pat. No. 4,663,727 in like manner teaches the use of an ultrasonic inspection apparatus for inspecting the condition of steam generating tubes from the interior of the tubes following insertion of and bonding of a repair sleeve within the tube. Inspection is for the purpose of discovering voids in the bonding, and is accomplished by a probe equipped with ultrasonic transducers, the probe being advanced internally longitudinally along the tube being inspected in increments of 0.032 of an inch and rotated at each plane to perform a circumferential scan of the tube to detect flaws in the bonding. The signals generated by the ultrasonic transducers are received, digitized and processed, with the aid of a programmed digital computer, to graphically display the existence and location of voids.

In U.S. Pat. No. 4,691,572, it is stated that in conventional ultrasonic transducer inspection of metallic objects, there is a requirement for the interposition of an acoustic coupling medium, usually liquid, between the transducer and the wall under inspection. This patent teaches an apparatus for the inspection of pipelines or tubing from the interior thereof, that utilizes "contactless" electromagnetic transducers that eliminate the need for a coupling medium between the transducer and the interior surface of the wall being inspected, while having the capability of generating ultrasonic waves within the material under inspection, for the detection of flaws therein.

U.S. Pat. No. 4,700,572 teaches a method and apparatus for automatic and continuous ultrasonic inspection of elongated steel pipes that are fed successively to the inspection station. The ends of each of the lengths of pipe are detected, the location of flaws in relation to the ends of the pipe are detected, and marking means are applied to the pipe to mark the location of each of the flaws.

U.S. Pat. No. 4,872,130 teaches the utilization of ultrasonic wheel probes comprising rotatably mounted transducer block and yoke assemblies to facilitate rapid adjustment of the helical scan angle of the assembly for use with different sized pipe, inspection of which proceeds through rotation of the pipe in relation to the transducer arrays, which move helically along the pipe from one end to the other. The system is coupled to a pair of computers, one being dedicated to user input/output, while the second computer controls real-time processing of ultrasonic data received from the transducers. The system has the capability of indicating pipe status through use of automatic color-coding, graphic presentation on a computer monitor or through printing of the results of the inspection.

U.S. Pat. No. 4,995,320 is directed to a carriage structure for providing mobility along the length of a steel pipe of the equipment or instruments utilized to effect inspection of the pipe for flaws. One of the advantages claimed for the carriage structure is that it does not surround the pipe but rather moves along the pipe on magnetized wheels that retain the carriage on the pipe, and a drive system that drives the carriage along the pipe longitudinally and which can be controlled to cause the carriage to move circumferentially about the outer surface of the pipe. Flaw detection sensors are stated as being capable of support on the carriage, with appropriate transmission of the signals from such flaw detector sensors to a signal converter and a data processing device, where the data regarding the flaws are processed, and presumably displayed and/or printed.

U.S. Pat. No. 5,043,663 is directed to a method and apparatus for detecting and displaying or printing the existence, location, and extent of all defects in a tubular member. A rotatable head supporting a multiplicity of transducers is caused to move along the length of the tubular member. Signals from the transducers are processed, preferably by a computer system, and indicate the presence of flaws and their physical characteristics. Longitudinal and circumferential position detectors cooperate with the transducers and the computer processing equipment to indicate the location and configuration of the defects in the tubular member.

It is significant to note that in all of the prior art patents listed above, and in known conventional inspection procedures, testing or inspection proceeds along surfaces that are smooth, i.e., surfaces that do not contain abrupt changes in direction or other surface irregularities. There is good reason for this phenomenon. The reason is that ultrasonic inspection of materials utilizing ultrasonic transducers that are in physical contact with the material under test, with or without a couplant, is carried out using transducers that generate a beam which is related to the surface of the material under test by a fixed angle. If the angle of the surface impinged by the beam changes abruptly, but the transducer generated beam angle does not change to compensate for the change in surface angle, the angle of the beam transmitted through the member under test and reflected back from a flaw or the opposite surface is also changed, resulting in portions of the material from which the member is fabricated to remain unexamined or not inspected, or inspected in an inferior manner, thus reducing the level of reliability of the test.

Accordingly, one of the important objects of the present invention is the provision of a method and apparatus for the accurate and reliable ultrasonic inspection of materials having irregular surfaces.

It is surprising that we have not discovered in the prior art any teaching of an ultrasonic transducer inspection system or apparatus in which the transducer ultrasonic beam direction of transmission is automatically altered when the surface angle of the member under test changes, to thus maintain constant the angle at which the ultrasonic beam penetrates the member under test and is reflected back from a flaw or the opposite surface. Accordingly, it is an important object of this invention to provide an ultrasonic transducer assembly possessing this capability.

Still another object of the invention is the provision of a variable angle ultrasonic transducer assembly which achieves angle variation in a simplified and novel configuration, utilizing the properties of a liquid ultrasonic couplant to provide a usable "footprint".

A still further object of the invention is the provision of a contact type ultrasonic transducer assembly which, when used in conjunction with an appropriate computer-driven scanning system, is capable of generating ultrasonic beams in the material under test at angles which are continuously variable during the course of the examination to compensate for irregularities in the surface of the material, thereby maintaining the beam angle transmitted through the material and reflected back at a constant angle, thus precluding failure to scan sections of the material.

Heretofore it has not been possible to adequately inspect tubular materials having irregular concentricity or variable wall thickness, such as tubular members having pipe weld overlays or pipe fittings such as reducers, couplings or valves and forgings. Accordingly, it is yet another object of the invention to provide an ultrasonic transducer assembly capable of generating a continually variable beam angle to accommodate irregularities of the type noted in the surface configuration of the member under test.

A still further object of the invention is the provision of an ultrasonic transducer operatively mounted for automatic computer-controlled rotational repositioning of the transducer to accommodate surface irregularities in the material being tested.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, in one aspect, the variable angle ultrasonic transducer of the invention comprises a piezo-electric element mounted within or in operative association with a delay line that is preferably formed from a synthetic resinous material such as that sold under the trademark "Lucite". The piezo-electric element constitutes a curved element having a predetermined radius, herein by way of example and not by limitation, a two inch radius of curvature, and embedded in the synthetic resinous delay line. The perimeter of the delay line remote from the piezo-electric element is formed with a curved surface that may have, for instance, a radius that is approximately one-half the radius of curvature of the piezo-electric element. While we have found this ratio to be useful, other ratios may of course be utilized under appropriate circumstances. Preferably, the body of synthetic resinous material forming the delay line, and within which the piezo-electric member is embedded, is captured between two laterally spaced plates, conveniently fabricated of aluminum in a circular configuration and having oppositely extending transducer pivot shafts projecting coaxially from the plates. Ultrasonic sound waves generated by the piezo-electric element are transmitted through the synthetic resinous material and emanate from the curved peripheral surface to impinge on the outer surface of the test piece. It is preferable that a liquid couplant be provided between the curved ultrasonic sound transmitting surface of the transducer and the outer surface of the test piece. The length of the synthetic resinous delay line of the transducer measured along the radius of the piezo-electric member is predetermined to provide an ultrasonic sound wave that is refracted and propagated by the liquid couplant at an angle of approximately twelve degrees, to thus produce a longitudinal wave (L-wave) of approximately 65 degrees propagated through a stainless steel test piece, for instance. Means are provided for exciting the piezo-electric member to create the ultrasonic sound wave, and means are also provided for longitudinal and vertical translation of the transducer assembly in relation to a test piece, and for effecting continual pivotal repositioning of the transducer head to accommodate irregularities in the surface of the test piece that cause vertical translation of the transducer, to thereby maintain constant the angle of incidence of the ultrasonic wave with respect to the internal diameter (I.D.) where the test piece is a tube, and the remote surface where the test piece is essentially flat, the test piece thus being tested accurately and reliably irrespective of outside surface irregularities of the test piece, which are accommodated by vertical and rotational repositioning of the transducer assembly.

BRIEF DESCRIPTION OF THE DRAWINGS

FIG. 3 is a diagrammatic end elevational view of the transducer assembly mounted in a holding fixture for pivotal repositioning about the center of curvature of the transducer "shoe".

FIG. 4 is a diagrammatic front elevational view of the mounted transducer assembly of FIG. 3.

DESCRIPTION OF THE PREFERRED EMBODIMENT

Figure 1:
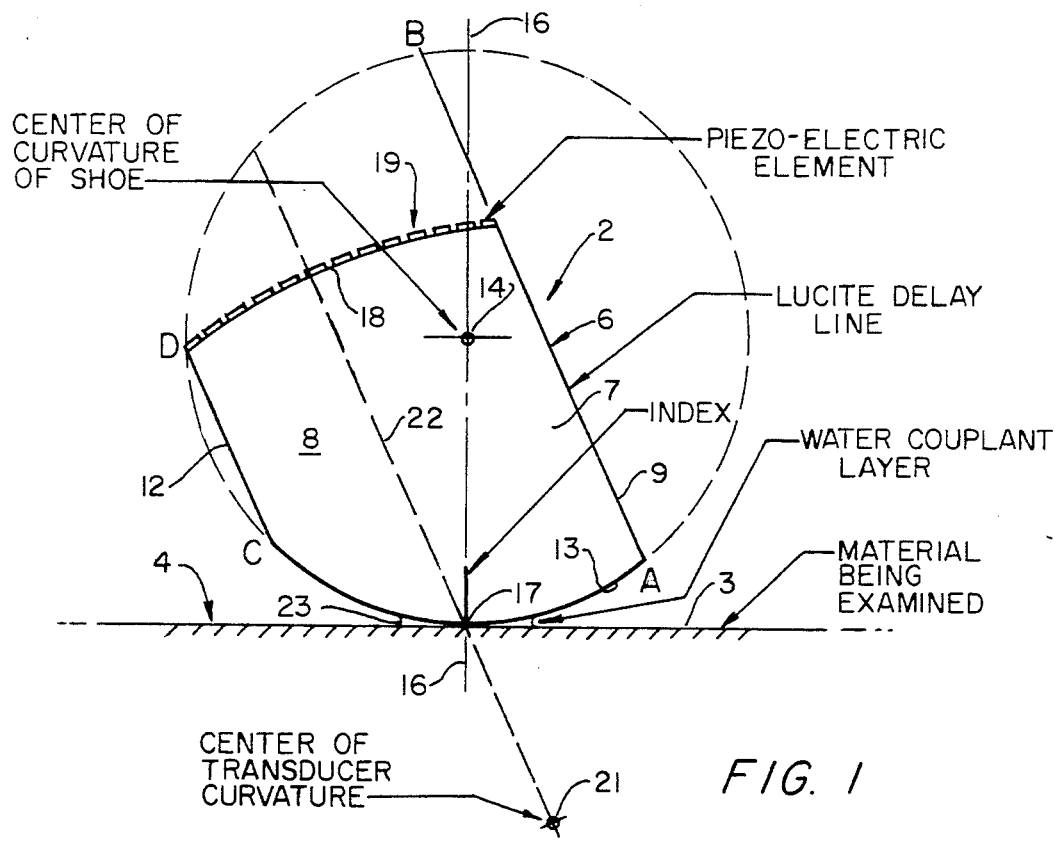
FIG. 1 is a schematic view of a piezo-electric member and a synthetic resinous delay line apart from other transducer control structures and associated with the surface of material to be examined.

In terms of greater detail, the variable angle ultrasonic transducer of the invention enables the accurate testing of metal objects in a manner and with a reliability factor not heretofore possible with conventional ultrasonic transducers. As indicated by the prior art patents cited above, and those that are listed in the prior art patents cited above, the broad concept of testing metallic structures, particularly tubular metallic structures such as pipe and conduits, is old in the art. However, as also indicated by the prior art patents listed above, innovations in structure and method have been contributed to the art to improve the techniques of testing, the facility with which such tests are conducted, and the reliability of the test results. Despite such innovations in structure and methods, it is surprising that no one heretofore appears to have conceived and/or reduced to practice an ultrasonic transducer that is particularly applicable to test metallic objects the surfaces of which are particularly irregular, such as, for example, the surface of a stainless steel pipe that has been welded so as to produce on the surface of the pipe irregular beads of welded material which must, nevertheless, be tested to determine their integrity.

It is of course well known in the art of ultrasonic testing of metallic objects, particularly steel pipe, but also other metallic bodies, such as steel railroad rails and steel beams for inclusion in high-rise buildings, that there are several different types of defects in steel members. Thus, with respect to steel pipe, which is usually tubularly cylindrical, having an outer peripheral surface (O.D.) and an inner peripheral surface (I.D), one such defect might be a sudden and not readily detected variation in the wall thickness of the pipe, thus altering the strength characteristics of the pipe. Another type of defect might be a void within the interior of the wall structure or body, not visible from the exterior or the interior, but again altering the strength characteristics of the pipe and perhaps resulting in its rupture to the detriment of property and people in the vicinity of the rupture. These defects may be very small and of negligible consequence, or they may be large and require repair or replacement of the entire member or the portion including the defect. In this regard, it is crucial to know the size and extent of the defect so that appropriate decisions may be made regarding the utilitiy of the member despite the defect, or its repair or replacement.

In the vernacular of ultrasonic testing of tubular members such as steel pipe, defects are usually defined as being longitudinal, i.e., extending in the direction of the long dimension of the member, or circumferential, i.e., extending about the longitudinal axis of the member, or as a wall thickness defect, or as a defect that extends through the material in a transverse direction and thus includes both circumferential and longitudinal characteristics. As indicated by the prior art, there are ultrasonic transducer testing devices that test for each of these defects individually and/or collectively in one or more passes over the member being tested, and which utilize computer technology to depict the defect on a computer monitor for visual analysis regarding size, shape and location, and which also provide a printed record of the defect, recording the various parameters required for an intelligent decision regarding use of the member having the defect. It is clear from the prior art patents listed above that these devices, systems and methods are all applicable to smooth-surfaced members being tested, and are not suitable for testing members having irregular surfaces because they are not continually adjustable to accommodate irregularities and the inherent change in the angle of propagation of the ultrasonic sound waves within the article or member being tested caused by the irregularity, resulting in a spurious and unreliable test result.

By constructing an ultrasonic transducer in a particular manner to transmit ultrasonic sound waves incident upon the member under test at a relatively small angle, say an angle of incidence of approximately twenty-four degrees, the result is that the ultrasonic sound waves are dispersed in the member under test in a much wider angle, in the order of approximately sixty-five degrees, thus increasing dramatically the volumetric increment of the material subjected to the test beam. Now, if this ultrasonic transducer is mounted in such a way that it may be automatically continually repositioned during a test without interruption of the test, as by sensing vertical displacement of the transducer with consequent automatic pivotal movement thereof, to compensate for irregularities in the surface of the member under test so that the angle of propagation of the ultrasonic test beam within the interior of the member under test is maintained constant despite the irregularity of the surface against which the transducer impinges, it will be seen that much more accurate and reliable test data will result. We have discovered that if the ultrasonic transducer of the invention is mounted for continual repositioning to accommodate irregularities in the manner indicated, it can also be connected to a computer system that receives signals correlated to the degree of axial and vertical displacement of the transducer, and which continually and automatically calculates the degree of rotational repositioning of the transducer required to accommodate the irregularity by maintaining the beam angle constant. It will thus be seen that an automatic system is provided that is capable of reliably and continually testing by ultrasonic transducer means metallic objects having both smooth and irregular surfaces.

Referring to the drawings, particularly the embodiment illustrated in FIG. 1, it will be seen that the ultrasonic transducer of the invention is illustrated schematically and designated generally by the numeral 2. The ultrasonic transducer is shown in relation to the surface 3 of a stainless steel test member designated generally by the numeral 4, which may be either flat or curved in the nature of a tubular stainless steel pipe. The ultrasonic transducer includes a delay line designated generally by the numeral 6, and formed from a body 7 of synthetic resinous material, conveniently such as that sold under the trademark "Lucite". The body of synthetic resinous material, for purposes of illustration only and not by way of limitation, is provided with opposite flat and parallel sides 8 intercepted fore and aft, respectively, by a front edge 9 spaced from and parallel with a rear edge 12. One end edge 13 of the body 7 constitutes an ultrasonic sound transmitting surface and is circularly arcuate about an axis of rotation 14 which, when extended, as shown in FIG. 4, passes through the body 7 perpendicular to the flat sides 8, parallel to the front and rear edge surfaces 9 and 12, nearer to the front edge surface 9 than to the rear edge surface 12, and lying in a plane 16 which, when extended, intersects the circularly arcuate sound transmitting surface 13 of the delay line at the index point or line 17 where the surface 3 of the material under test is tangent to the circularly arcuate ultrasonic sound transmitting end edge surface 13 of the synthetic resinous delay line. It will of course be understood that the delay line may take various configurations without departing from the spirit of the invention.

As illustrated in FIG. 1, if a circle, shown in broken lines, is defined about the axis of rotation 14, the circularly arcuate ultrasonic sound transmitting end surface 13 of the delay line coincides with the outer periphery of the circle, and is normally generally bisected by the plane 16 that is perpendicular to the surface 3 of the test member. Another relationship that is apparent in this specific embodiment is that the front edge surface 9 lies at an angle of approximately twenty-four degrees to the plane 16 that passes through the center of rotation 14 and the index point 17. The front edge surface 9, extended, thus defines a chord intercepting the circle at A and B, the chord thus subtending the arc AB. In like manner, the rear edge surface 12, without need of extension, intercepts the circle at C and D, thus subtending the arc CD.

Figure 2:
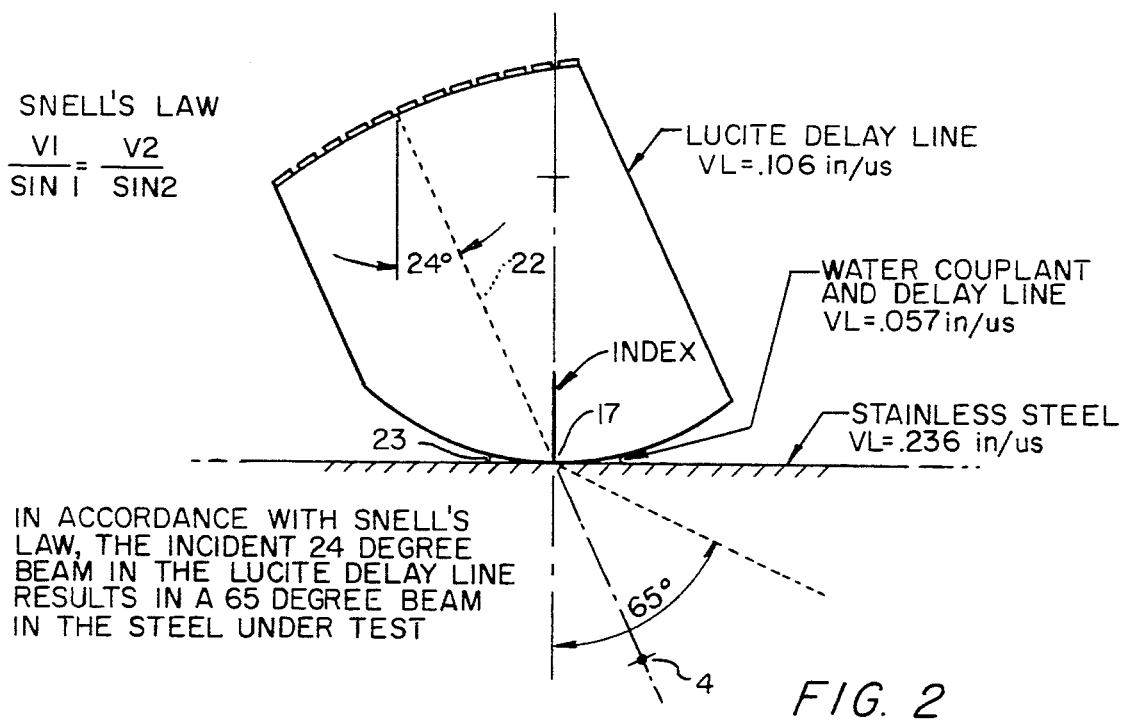
FIG. 2 is a schematic view similar to FIG. 1, but illustrating representative angular relationships between the center of curvature of the piezo-electric member, the center of curvature of the ultrasonic sound transmitting surface of the delay line, and the index point of the transducer "shoe".
Figure 5:
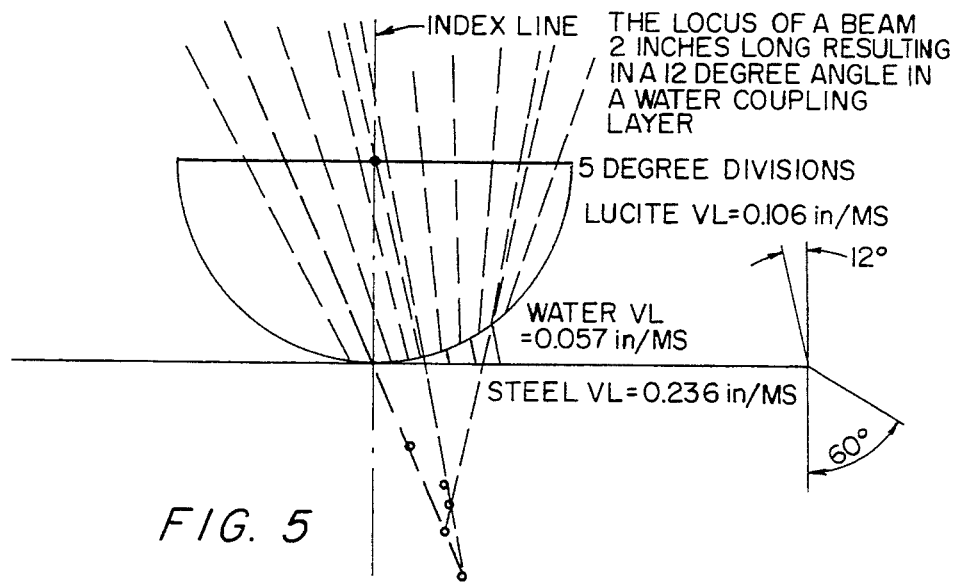
FIG. 5 is a schematic view illustrating that the transducer may be shaped differently from the illustration in FIGS. 1 and 2, and positioned so that the ultrasonic sound waves pass through the couplant and impinge on the material under test in parallel rays to thereby increase the effective contact area of the transducer to include an extended couplant interface.

It should be understood that the description of the transducer illustrated in FIGS. 1 and 2 and in more detail in FIG. 3, constitutes a specific configuration actually constructed and tested and found to provide satisfactory results. In this specific construction, the end edge 18 of the delay line 6, opposite the transmitting end edge 13, is circularly arcuate and capped by a piezoelectric element designated generally by the numeral 19, in this embodiment the piezo-electric member being designed to oscillate in a frequency range of from 0.5 MHz to 25 MHz. As illustrated in FIG. 1, the piezoelectric member 19 is curved about a center of curvature 21 that is spaced from the transmitting end 13 of the transducer and which is included in a plane that passes through the index point 17 and lies parallel to the front and rear edges 9 and 12 of the synthetic resinous delay line 7. We have found that it is advantageous for reliable and accurate testing of stainless steel to produce a 65 degree L-wave in the stainless steel. To accomplish this, we have found that there is an important relationship between the curvature of the piezo-electric member, the index point or line 17 at which the untrasonic transmitting end edge 13 contacts the test piece, and the position of the center of curvature of the piezo-electric member 19 in relation to the index point 17. Thus, in the embodiment illustrated in FIG. 1, we have found that if the curved piezo-electric member 19 is placed the same distance from the center of curvature as its radius, then the majority of the refracted beam in the stainless steel will be substantially a 65 degree L-wave. To accomplish this object, we have determined that the true location of the center of curvature 21 of the piezo-electric member is determined by multiplying the sine of the L-angle (65 degrees) by the radius of the shoe surface 13 to derive the distance from the index point 17 at which the center of curvature 21 will lie along the plane that includes both the center of curvature 21 and the index point and which constitutes the radius of the curvature of the piezo-electric member. Thus, for a piezo-electric member that is placed 5.08 cm from the center of curvature 21, we have found that the distance of the center of curvature 21 from the index point 17 amounts to approximately 2.199 cm. It should of course be understood that these calculations are made for a specific transducer construction, and that other dimensions appropriate to different size transducers having different radiuses of curvature will result in a different dimension for location of the center of curvature 21 from the index point 17.

Referring to FIG. 2, it is customary in the industry to use a couplant medium between the ultrasonic transmitting end edge 13 of the transducer and the surface 3 of the material being tested. Such a couplant might, for instance, be a liquid such as water, or some other appropriate liquid or other material that has the same or substantialy similar longitudinal velocity as water. Considering that the couplant 23 in FIGS. 1 and 2 constitutes water, we have found that if the angle of the plane 22 passing through the center of curvature 21 and the index point 17 lies 24 degrees from a vertical plane 16 that includes the center of curvature 14 of surface 13 and the index point 17, the ultrasonic sound waves emanating from the transmitting surface 13 are refracted and pass through the water couplant at an angle of 12 degrees. We have found that this condition results in the propagation in the stainless steel test member 4 of an ultrasonic beam that proceeds at a 65 degree angle to the vertical plane 16 that passes through the center of curvature 14 of the transmitting end edge 13 and the index point 17. These results have been achieved utilizing a synthetic resinous delay line 6 having a longitudinal velocity of 0.269 cm/μs, a water couplant and delay line longitudinal velocity of 0.145 cm/μs, and a stainless steel test piece having a longitudinal velocity of 0.599 cm/μs. Stated simply, in accordance with Snell's law of $V^1/\text{Sin } 1 = V^2/\text{Sin } 2$, the incident 24 degree beam in the delay line results in a 65 degree beam in the stainless steel member under test.

Figure 7:
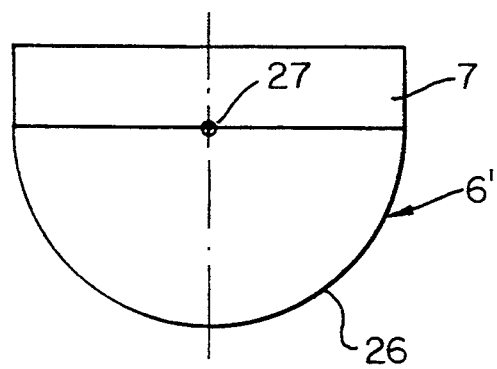
FIG. 7 is a schematic view of a second embodiment of a piezo-electric member and synthetic resinous delay line of different configuration from that illustrated in FIG. 1, and shown to emphasize that the configuration of the delay line in FIG. 1 is merely to facilitate an explanation of the principles involved and not by way of limitation.

In order to accomplish the purpose intended for the ultrasonic transducer of the invention, it is preferable that the transducer be capable of translation longitudinally along the length of a test piece, or circumferentially thereabout, and that it also be capable of rotation about the center of curvature of the transmitting shoe surface 13. In addition, the ultrasonic transducer must be capable of being elevated by a surface irregularity in relation to its "home" position on a smooth surface of the piece under test, and these conditions are illustrated diagrammatically in FIG. 8 of the drawings. While we have shown the configuration of the transducer in FIG. 8 to be similar to the configuration of the transducer illustrated in FIGS. 1 and 2, it should be understood that the transducer may take a different configuration, such as the configuration illustrated in FIG. 7, where the shoe 6', constituting a synthetic resinous delay line similar to the delay line 6 of FIG. 1, is provided with a half-round or semi-circular ultrasonic sound transmitting surface 26 supported in a metallic case 27, the semi-circular ultrasonic transmitting edge 26 having a center of curvature and of rotation 27.

Again referring to FIG. 8, it will be seen that in position (A), where the ultrasonic transmitting surface 13 rests on relatively smooth surface 3 of the stainless steel test member designated generally by the numeral 4 in its "home" position, the center of rotation 14 of the delay line 7 is as illustrated in FIG. 1, with the plane 22 and the front and rear edges 9 and 12, respectively, of the delay line lying at an angle of 24 degree from the vertical plane 16 that passes through the center of curvature of the surface 13 and the index point 17. However, in position (B) it will be seen that the ultrasonic transducer has been translated to the right along the irregular surface 3 of the test member and that the transducer has been elevated to accommodate the surface irregularity in the form of a protrusion from the surface 3, and has been rotated clockwise about the center of curvature and axis of rotation of the ultrasonic transmitting surface 13 so that the 12 degree angle of the ultrasonic sound waves passing through the water couplant impinge on the surface of the stainless steel test member, albeit irregular, at a 12 degree angle, thus again generating a 65 degree L-wave in the body of the stainless steel test member.

We have found that the rotational repositioning of the transducer to accommodate irregularities may be continually controlled through appropriate computer technology that receives signals correlated to the axial and vertical motion of the transducer and automatically varies the angle of rotation of the transducer to maintain the angularity of the 65 degree beam desired to be propagated in the test piece. This constancy of the L-angle of 65 degrees is achieved by actuation of a computer controlled linear actuator, as will hereinafter be explained, which continually controls the rotational repositioning of the ultrasonic transducer during the test procedure in correlation with its elevation in relation to the "home" position and without interruption of the test procedure.

To construct a practical and utilitarian transducer assembly, reference is made to FIG. 3 wherein the transducer illustrated in FIGS. 1 and 2, mounted as a side-by-side pair, have been mounted between two circular metallic plates 26 and 27, the center of rotation of the plates being coincident with the axis line 14 which constitutes the center of curvature and rotation of the ultrasonic transmitting surface 13 of the transducer. In this embodiment, the radius of the plates 26 and 27 was 2.22 cm and each of the plates is provided with oppositely extending and coaxially aligned mounting bosses 28 and 29, respectively, as shown, each boss having a radius of 0.635 cm. These axially aligned bosses 28 and 29 constitute mounting axles for the assembly, it being noted that each of the two side-by-side mounted transducers 2 and 2' (FIG. 4) have a thickness of approximately 1.587 cm and are spaced apart approximately 0.0635 cm by an appropriate sound insulator 31, such as a layer of cork. This insures that the ultrasonic transmission of each of the transducers will be independent of the ultrasonic transmission of the other, while the ultrasonic transmission of both will effect testing of a broader area of the member under test. It should also be noted that in this embodiment, the sides 8 of each of the transducers associated adjacent the circular plates 26 and 27 are insulated from the associated plate by an appropriate insulator layer 32 of cork or other suitable sound absorbing material so as to preclude transmission of ultrasonic sound waves or beams into the metallic plates 26 and 27.

Referring to FIG. 3, it will be noted that in this embodiment, the contact surface 13 of the transducer is 2.413 cm from the center of rotation 14, and that the radius of the focussed transducer element 19 is 5.08 cm and located along the plane 22 that passes through the center of curvature of the focussed transducer element 19 and the index point 17 at which the plane crosses the point of tangency of the transmitting surface 13 with the surface of the material under test. It should also be noted that these parameters result in the center of curvature of the focussed transducer element 19 being positioned approximately 1.648 cm from the point of tangency, measured along the vertical plane 16 that passes through the center of curvature of the transmitting surface 13 and the index point 17. Again, while these dimensions and configurations have been found to be satisfactory in actual constructions that have been tested, it is apparent that other configurations and dimensions may be utilized depending upon the circumstances under with the ultrasonic transducer must be utilized. To activate the piezo-electric element, a "pitch/catch" (P/C) Microdot system 33 is opertively mounted between the two plates 26 and 27 as shown in FIG. 3, and operatively related also to the piezo-electric element 19. Since the Microdot system 33 is state-of-the art and commercially available, in the interest of brevity in this description, such system will not be described.

Figure 6:
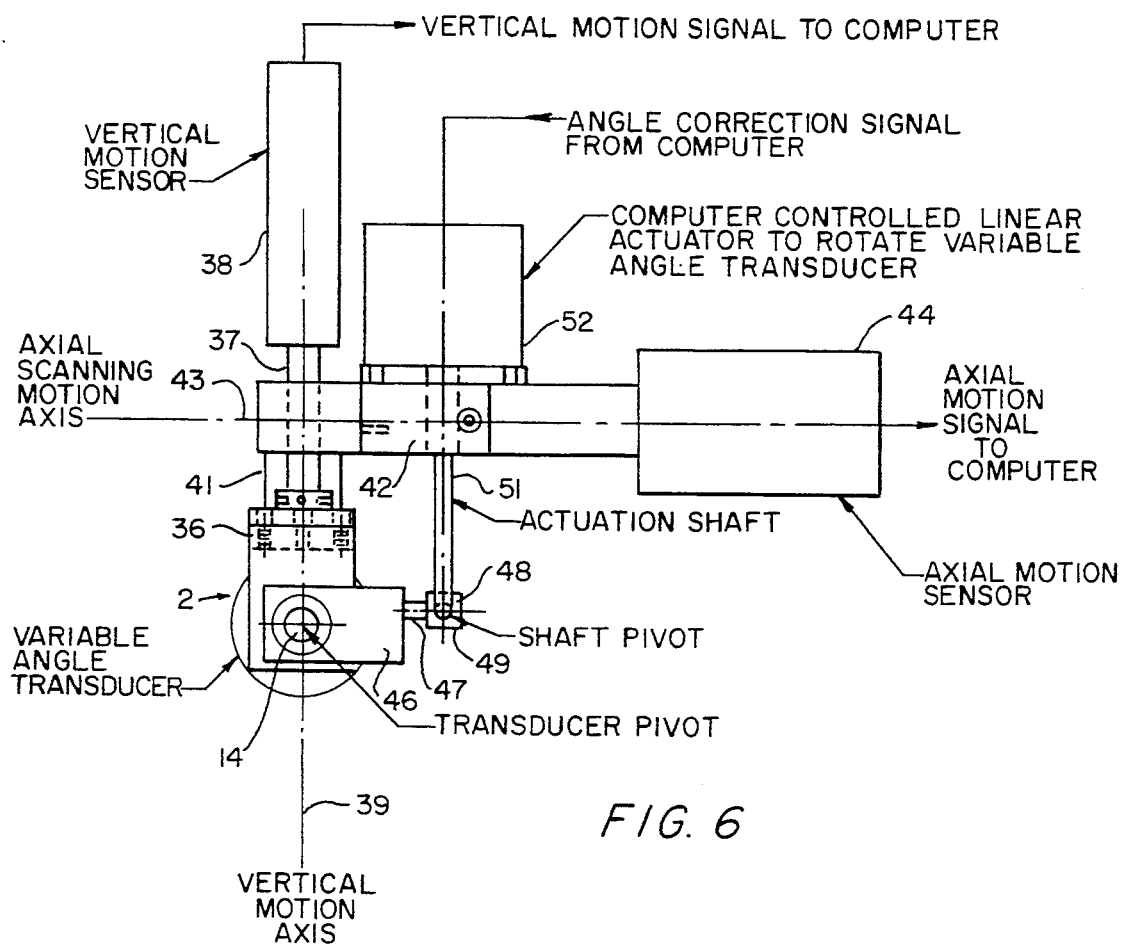
FIG. 6 is a diagrammatic view illustrating the variable angle ultrasonic transducer mounted in association with means for sensing and transmitting to a computer signals correlated to the axial and vertical motion translation of the transducer in relation to a test piece to enable continual variation of the angle of the transducer in response to angle correction signals derived from the computer.

To effect continual and automatic rotational repositioning of the ultrasonic transducer, means under control of an appropriate computer (not shown) has been devised and illustrated in FIG. 6. As there shown, a variable angle transducer designated generally by the numeral 2, and constituting the assembly illustrated in FIG. 3, is rotatably mounted by means of the bosses 28 and 29 on a bracket member 36, connected by an appropriate shaft 37 to a vertical motion sensor 38 that generates a vertical motion signal that is sent to the computer. The vertical motion sensor is mounted coaxially with respect to a vertical motion axis 39 that is perpendicular to the axis or center of rotation 14 of the bosses 28 and 29 as shown. Also mounted on the bracket 36 is a bracket 41 extending upwardly from the bracket 36 and connected to a horizontal beam 42 having an horizontal axial scanning motion axis 43, the beam 42 being connected at its end remote from the bracket 41 to an axial motion sensor 44 that senses axial movement of the transducer and transmits an axial motion signal to the computer. These vertical and axial motion signals are stored in the computer and acted upon when necessary by the computer to control the rotational repositioning of the transducer to ensure against variation of the predetermined angulation of the L-wave dispersed through the material being tested despite any surface irregularities that might be encountered by the transducer.

Figure 8:
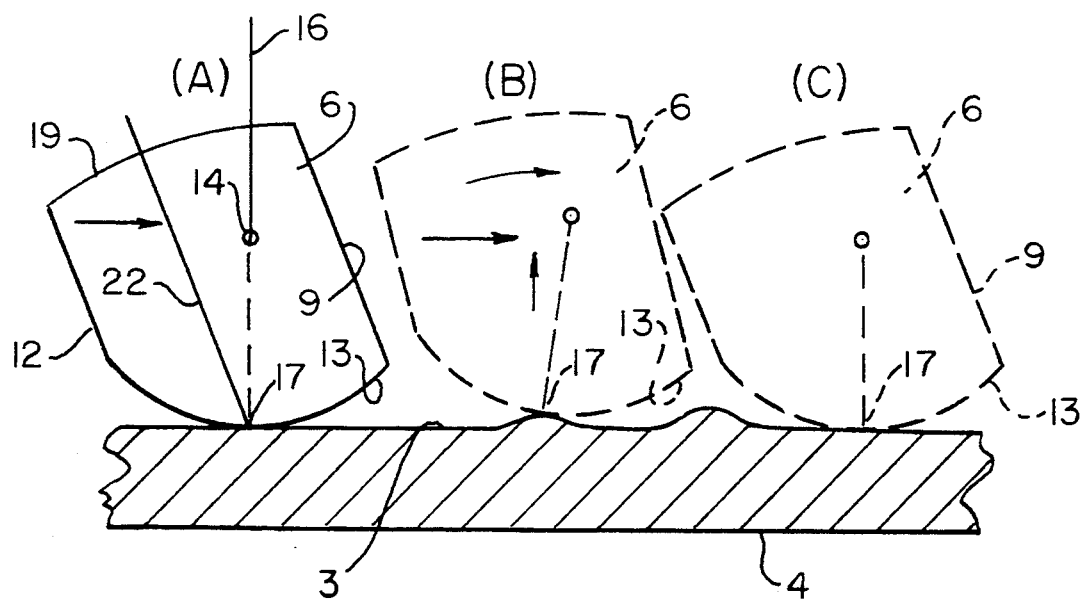
FIG. 8 is a diagrammatic view illustrating the axial, vertical and rotational repositioning of the transducer head that occurs in relation to a test piece having an irregular outer surface.

To effect pivotal repositioning of the transducer, as illustrated in FIG. 8, there is mounted on the bosses 28 and 29, as shown in FIG. 6, a yoke 46 that is either press-fitted on the bosses, or secured thereto by appropriate keys in conjunction with set screws (not shown) so as to prevent relative rotation between the yoke 46 and the bosses. Extending from the base of the yoke 46 is a shaft 47 having an enlargement 48 thereon, the shaft 47 and the enlargement 48 being arranged symmetrically about a horizontal axis. Pivotally mounted in the enlargement 48 is a pivot shaft 49, and connected to the pivot shaft is an actuator shaft 51. As shown, the actuator shaft 51 extends vertically from the pivot shaft 49, and terminates in a computer controlled linear actuator that functions, upon appropriate signals from the computer, to elevate or lower the actuator shaft 51, to thus impose a rotary moment on yoke 46 and the transducer assembly, causing it to pivot to vary the angle of the transducer in relation to the angle correction signals received from the computer.

It will thus be seen that as the transducer is translated axially, say to the right as viewed in FIG. 6, its incremental horizontal movement is detected or sensed and an axial motion signal is sent to the computer. When the transducer encounters an irregularity in the surface of the member being tested, causing it to be elevated as in FIG. 8(B), the elevation of the transducer in relation to its "home" position is sensed by the vertical motion sensor 38 and another signal representing the vertical motion of the transducer is sent to the computer. In concert with these two motions (vertical and horizontal) and the signals that are transmitted to the computer, the computer calculates the degree of rotation required to be imposed on the transducer assembly to effectively prevent a variation of the predetermined angulation of the L-wave dispersed through the material under test, and sends appropriate angle correction signals to the linear actuator 52 to control elevation or lowering of the shaft 51 to pivot the transducer about the axis 14 so as to maintain the 65 degree dispersion of the ultrasonic sound beams within the test member.

Having thus described the invention, what is believed to be new and novel and sought to be protected by letters patent of the United States is as follows.

We claim:

1. The process of inspection of metallic objects normally having a surface regularity adhering to a predetermined standard of normalcy and including geometric and surface irregularities varying from said standard of normalcy to discover an abnormality therein and display and/or record the position and nature of the abnormality, comprising the steps of:
    a) generating ultrasonic sound waves in a transducer adapted to impinge on a metallic object;
    b) transmitting said ultrasonic sound waves into said metallic object under inspection at a predetermined angle correlated to a surface regularity adhering to said predetermined standard of normalcy;
    c) receiving and displaying a reflection of said ultrasonic sound waves propagated within said metallic object to indicate the presence of an abnormality in said metallic object;
    d) detecting in a continuous manner the surface irregularities on said metallic object under inspection;
    e) measuring in units of length the extent of variation of said detected surface irregularities in relation to said surface regularity adhering to said predetermined standard of normalcy;
    f) converting into electrical signals said measured variation of the surface irregularities from said predetermined standard of normalcy thereof;
    g) applying said electrical signals to variably control the rotational repositioning of said transducer in relation to the surface of said metallic object being inspected whereby said predetermined angle of propagation of said ultrasonic sound waves within said metallic object are maintained constant despite said surface irregularities whereby abnormalities in said metallic body are reliably and accurately detected and displayed; and
    h) wherein said surface irregularities are detected by impingement of the transducer thereagainst and displacement of the transducer thereby.

2. The process according to claim 1, wherein the extent of variation of said detected surface irregularities is measured by variable vertical displacement of the transducer as the transducer encounters, impinges against and passes over the irregularities, and generating an electrical signal correlated to said vertical displacement of the transducer to control the rotational repositioning of the transducer during passage over the irregularities.

3. The process according to claim 1, wherein said sound waves are generated by a piezo-electric member selectively operable in a frequency range between 0.5 MHz and 25.0 MHz.

4. The process according to claim 1, wherein said sound waves are generated by a piezo-electric member operated at a frequency of 2.25 MHz.

5. The process according to claim 1, wherein said sound waves are propagated in said metallic object at a predetermined angle of 65 degrees.

6. The process according to claim 1, wherein said transducer transmits ultrasonic sound waves at a predetermined angle into a liquid couplant interposed between the transducer and the surface of said metallic object whereby said sound waves are refracted by said liquid couplant and impinge on the surface of said metallic object at a second predetermined angle from whence said sound waves are refracted by and propagated through said metallic object at a third predetermined angle.

7. The process according to claim 6, wherein said sound waves are transmitted through said liquid couplant at a predetermined angle of 12 degrees.

8. The process according to claim 6, wherein said sound waves passing through said liquid couplant impinge on the surface of said metallic object at an angle of 12 degrees.

9. An ultrasonic test probe for generating ultrasonic sound waves for transmission into metallic objects to inspect for abnormalities therein, comprising:
   a) at least one transducer, wherein said at least one transducer comprises:
      i) a piezo-electric member operable at a selected frequency in a range between 0.5 MHz and 25 MHz;
      ii) a synthetic resinous delay line having first and second ends and operatively associated at said first end with said piezo-electric member and at said second end having an arcuate sound transmitting end surface adapted to transmit ultrasonic sound waves into a metallic object under inspection;
   b) frame means encasing said at least one transducer and including oppositely extending bosses symmetrical about a rotative axis constituting the center of curvature of said arcuate sound transmitting end surface of the delay line; and
   c) means supporting said at least one transducer and said frame means for axial and vertical displacement in relation to said metallic object under inspection at a point of tangency of said metallic object with said arcuate sound transmitting end surface and rotational displacement of said arcuate sound transmitting end surface in correlation to said vertical displacement.

10. The combination according to claim 9, wherein said piezo-electric member possesses a predetermined radius of curvature, and the operatively associated end of the delay line conforms to the curvature of the piezo-electric member.

11. The combination according to claim 9, wherein said arcuate sound transmitting end surface is circularly arcuate, and the center of curvature of said arcuate sound transmitting surface is coincident with a plane that substantially bisects said arcuate end surface when extended perpendicularly to the surface of said metallic object under inspection.

12. The combination according to claim 9, wherein said frame means includes a pair of spaced metallic plates having mutually symmetrical opposed arcuate perimeter portions corresponding in curvature to the curvature of said arcuate sound transmitting end surface.

13. The combination according to claim 9, wherein said means supporting said at least one transducer and said frame means for axial and vertical displacement in relation to said metallic object includes a bracket rotatably mounted on said oppositely extending bosses, a vertical motion sensor connected to said bracket and operative to signal the extent of vertical movement of said at least one transducer, a yoke non-rotatably mounted on said oppositely extending bosses, a linear actuator connected to said yoke and operative to rotationally reposition the arcuate sound transmitting surface of said at least one transducer in response to said vertical motion signals, and an axial motion sensor connected to said bracket and operative to signal the extent of axial movement of said at least one transducer in relation to the metallic object being inspected.

14. The combination according to claim 9, wherein said arcuate sound transmitting end surface is circularly arcuate, and the center of curvature of said arcuate sound transmitting end surface is coincident with a plane which when extended intersects said arcuate sound transmitting end surface at the point of tangency of the surface of said metallic object with said circularly arcuate transmitting end surface of the delay line.

15. The combination according to claim 10, wherein the center of curvature of said piezo-electric member lies in a plane which when extended intersects said circularly arcuate sound transmitting surface at the point of tangency of the surface of said metallic object with said circularly arcuate transmitting end surface of the delay line, said center of curvature of said piezo-electric member being spaced on the opposite side of said surface of said metallic object from said piezo-electric member.

16. The combination according to claim 9, wherein said piezo-electric member possesses a radius of curvature the center of curvature of which lies in a plane which when extended passes through the point of tangency of the surface of said metallic object with said arcuate sound transmitting end surface of the delay line, said center of curvature lying on the opposite side of said point of tangency from said piezo-electric member.

17. The combination according to claim 9, wherein said arcuate sound transmitting end surface possesses a radius of curvature the center of curvature of which is coincident with a first plane which when extended includes the point of tangency of the surface of said metallic object with said circularly arcuate ultrasonic sound transmitting surface, said piezo-electric member possesses a radius of curvature the center of curvature of which is coincident with a second plane which when extended intersects said first plane at said point of tangency, and the centers of curvature coincident with said first and second planes are spaced on opposite sides of said point of tangency.

18. The combination according to claim 17, wherein said first and second planes when extended intersect at said point of tangency at an angle of approximately 24 degrees.

19. The combination according to claim 17, wherein said delay line includes front and rear edges parallel with said second plane and intercept said first and second ends of said delay line.

20. The combination according to claim 17, wherein said center of curvature of said piezo-electric member is spaced from said point of tangency a distance equal to the sine of 65 degrees multiplied by the radius of curvature of said arcuate ultrasonic sound transmitting end surface.

21. The combination according to claim 9, wherein said means supporting said at least one transducer and said frame means includes a bracket member on which said oppositely extending bosses are rotatably journaled, vertical motion sensor means connected to said bracket member and operable to sense vertical displacement of said at least one transducer resulting from contact of said arcuate ultrasonic sound transmitting surface with irregularities on the surface of said metallic member and to transmit a vertical motion signal to a computer, axial motion sensor means connected to said bracket member and operable to sense and transmit an axial motion signal to a computer to control axial displacement of said at least one transducer along said metallic object, and a linear actuator connected to said frame means encasing said at least one transducer and operable in response to computer controlled signals correlated to said vertical and axial motion signals to rotate said at least one transducer to maintain constant the angle of incidence of said ultrasonic sound waves transmitted into said metallic object despite the irregularities in the surface of said metallic object over which the probe is translated.

* * * * *